(12) United States Patent
Bratescu et al.

(10) Patent No.: US 7,338,538 B2
(45) Date of Patent: Mar. 4, 2008

(54) COMPOSITIONS AND METHODS FOR DARKENING KERATINOUS FIBERS

(75) Inventors: Daniela Bratescu, Northport, NY (US); Isaac D. Cohen, Brooklyn, NY (US); John Dudley Dreher, Sayville, NY (US); Monica Apostol, Coram, NY (US)

(73) Assignee: ELC Management LLC, Melville, NY (US)

(*) Notice: Subject to any disclaimer, the term of this patent is extended or adjusted under 35 U.S.C. 154(b) by 316 days.

(21) Appl. No.: 11/214,084

(22) Filed: Aug. 29, 2005

(65) Prior Publication Data

US 2007/0044248 A1    Mar. 1, 2007

(51) Int. Cl.
*A61K 7/13* (2006.01)
(52) U.S. Cl. .............. 8/405; 8/498; 8/614; 8/615; 8/617; 424/70.1; 132/202; 132/208
(58) Field of Classification Search ............... 424/70.1; 8/405, 498, 614, 615, 617; 132/202, 208
See application file for complete search history.

(56) References Cited

U.S. PATENT DOCUMENTS

| 6,224,851 | B1 | 5/2001 | Bara |
| 6,251,375 | B1 | 6/2001 | Bara |
| 6,264,933 | B1 | 7/2001 | Bodelin et al. |
| 6,352,699 | B1 | 3/2002 | Mondet et al. |
| 6,399,080 | B1 | 6/2002 | Bara |
| 6,573,235 | B1 | 6/2003 | Surbled et al. |
| 2002/0172696 | A1 | 11/2002 | Ferrari |
| 2004/0151679 | A1* | 8/2004 | Mogilevich ............. 424/70.1 |

OTHER PUBLICATIONS

Tuminello, et al.; Characterization of a Perfluorotetradecahydrophenanthrene Oligomer; Analytical Chemistry; vol. 67; pp. 1955-1962; Jul. 1, 1995.

* cited by examiner

*Primary Examiner*—Eisa Elhilo
(74) *Attorney, Agent, or Firm*—Yongzhi Yang

(57) ABSTRACT

The present invention provides a cosmetic or pharmaceutical composition and methods for coating keratinous fibers, whereby the composition comprises more than 50% of at least one perfluoro compound.

27 Claims, No Drawings

COMPOSITIONS AND METHODS FOR DARKENING KERATINOUS FIBERS

FIELD OF THE INVENTION

The present invention relates to cosmetic and pharmaceutical compositions. More specifically, the invention provides novel cosmetic compositions and methods for darkening keratinous fibers.

BACKGROUND OF THE INVENTION

It is often preferred to darken the keratinous fibers of the skin, especially the lashes above the eyes or eyebrows. Traditional methods include incorporating pigments in compositions to darken the fibers. Most commonly, carbon black was used as pigment to achieve the darkest black color for the keratinous fibers. However, due to safety restrictions, consumers are seeking compositions without carbon black to achieve the darkest black color. Manufactures have thus used various combinations of pigments to try and achieve such a black color. However, pigments tend to cause clumping and smudging once applied onto the keratinous fibers.

Perfluoro compounds have been used in cosmetic compositions as drying agents, anti-transfer agents, and as a solvent in mascara compositions. For example, U.S. Pat. No. 6,264,933 issued to Bodelin et al., teaches compositions for coating keratin fibers, particularly eyelashes, comprising a lamellar filler, an aqueous phase dispersed in a liquid fatty phase containing at least one volatile organic solvent such as perfluorocarbons. In U.S. Publication No. 20020172696, an anhydrous mascara composition comprising a nonvolatile perfluorocarbon and film-formers in the absence of pigments is disclosed. The publication limits the amount of nonvolatile perfluorocarbons to less than 50% by weight and discloses a specific group of film-formers. The publication does not teach or suggest that the composition darkens the keratinous fibers in any manner. In fact, the publication only teaches that the composition has the benefits of transfer-resistance, long wearing nature and gloss appearance. The Publication further notes that pigments may be added if desired for color.

Therefore, there remains a need for a suitable substitute for pigments for use in darkening keratinous fibers.

SUMMARY OF THE INVENTION

The present invention provides a cosmetic or pharmaceutical composition for coating keratinous fibers, whereby the composition comprises more than 50% of at least one perfluoro compound.

In an alternate embodiment, the present invention provides a cosmetic or pharmaceutical composition for coating keratinous fibers comprising at least 50% of at least one perfluoro compound and at least one perfluorocarbon film-former. The perfluorocarbon film-former is preferably a fluorinated oligomer.

In an alternate embodiment, the present invention provides a method of darkening keratinous fibers comprising applying to the keratinous fibers a composition comprising at least one perfluoro compound.

DETAILED DESCRIPTION OF THE INVENTION

Except in operating and comparative examples, or where otherwise explicitly indicated, all numbers in this description indicating amounts or ratios of material or conditions of reaction, physical properties of materials and/or use are to be understood as modified by the word "about." All amounts are by weight of the final composition, unless otherwise specified.

Specular reflection is light directed in an angle that is exactly opposite to the angle of incidental light. Such specular reflection is perceived as gloss or shine. It is believed that a high gloss sample would appear to be darker in color than an identical pigment sample with lower gloss. It is further believed that in order to achieve a dark color on keratinous fibers, a composition must impart a low refractive index while maintaining a specific specular reflection. Therefore, while not wishing to be bound by any theories, the darkest black color can be achieved using compounds with low refractive indexes and high gloss.

It has been unexpectedly discovered that certain perfluoro compounds create a darkening of keratinous fibers upon application, in the absence of pigments, as shown in FIG. 1. The perfluoro compounds unexpectedly reduce the L value, which represents lightness, when applied to the fibers. L value is measured using a spectrophotometer or a calorimeter.

The perfluoro compounds of the present invention can be selected from among several different perfluorocarbons. In a preferred embodiment, the perfluorocarbon may be a perfluorocycloalkane. Compounds of this type are commercially available from F2 Chemicals, Ltd. under the trade name FLUTEC™. These products come in a variety of forms, which differ from each other in molecular weight and viscosity, and relative volatility. Generally speaking, the molecular weights range from about 300 to about 800, with vapor pressures in the range of from <0.1 mbar up to about 500 mbar, and boiling points in the range of from about 45° C. to about 260° C. The preferred compounds of this type are those in the mid-range of viscosity and volatility, i.e. those having a molecular weight of between about 400 to about 650, vapor pressures of about <1 to about 50 mbar, and boiling points ranging from about 100° C. to about 220° C. Particularly preferred compounds of this type are perfluoro-1,3-dimethylcyclohexane, known as FLUTEC™ PC3, perfluorodecalin, sold as FLUTEC™ PC6, perfluoromethyldecalin, sold as FLUTEC™ PP9, and perfluorohydrophenanthrene, sold as FLUTEC™ PC11.

Although the perfluorocycloalkanes are particularly preferred, there are other groups of perfluoro compounds that can also be used, such as hydrofluoroethers.

Compounds of this type are disclosed, for example, in FR 2771290, the contents of which are incorporated herein by reference. The formula of such hydrofluoroethers is as follows:

$$CH_3-(CH_2)_n-[Z]_t-X-CF_3$$

wherein t is 0 or 1; n is 0, 1, 2 or 3; X is a linear or branched divalent perfluoroalkane radical having 2 to 5 carbon atoms, and Z is O, S or NR, wherein R is hydrogen, or a radical $-(CH_2)_n-CH_3$ or $-(CF_2)_m-CF_3$, where m is 2, 3, 4 or 5. Preferably, Z is O, and t is 1. Specific examples of these types of compounds are methoxynonafluorobutane, ethoxynonafluorobutane, or propoxy-undecafluoropentane. Such compounds are available commercially from 3M or Archimex under the designation "HFE".

An additional example of perfluorocarbons are perfluoroalkanes having the formula

$$CF_3-(CF_2)_n-CF_3$$

wherein n is an integer from 2-6. Examples of such compounds include dodecafluoropentane and tetradecafluorohexane.

Yet another example of perfluoro compounds are perfluoropolyethers having the formula

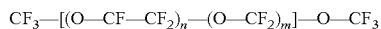
$$CF_3-[(O-CF-CF_2)_n-(O-CF_2)_m]-O-CF_3$$

Wherein m, n integers giving a molecular weight of 500 to 10,000. An example of such a compound is a polyperfluoromethylisopropyl ether such as Fomblin® HC25.

In one embodiment, the perfluoro compounds can be used alone as a clear coat for darkening keratinous fibers such as the hair and lashes. In this embodiment, the perfluoro compound is preferably relatively non-volatile, for example, polyperfluoromethylisopropyl ether or perfluorohydrophenanthrene. However, more frequently, the perfluoro compounds will be combined with additional components for ease of application and retention on the keratinous surface, and in these cases, the perfluoro compound(s) is in an amount of from more than 50% up to about 90%.

As an example of an additional component that may enhance the performance of the perfluoro compound, the composition may contain one or more perfluorocarbon film-formers, for example, perfluoro oligomers. Oligomeric byproducts are generally known, and are known to be useful as good atmospheric pressure solvents for PTFE. In the present invention, it has been surprisingly found that addition of an oligomeric byproduct as a perfluorocarbon film-former surprisingly enhances the darkening effect of the perfluorocarbon, while aiding in adhesion of the perfluoro compound to the keratinous fibers upon application, as shown in Example 2 below. It is particularly useful to employ such oligomers when the base perfluoro compound is relatively volatile.

Although it is contemplated that any perfluorocarbon film-former may be used, in the preferred embodiment, the perfluorocarbon oligomeric byproducts of the monomer perfluorotetradecahydrophenanthrene (C14F24), sold commercially under the tradename Flutec PP11). The oligomeric perfluorocarbons of the present invention have the general structural framework with the chemical formula C14F23 (C14F22)nC14F23, where n=0, 1 and 2 for dimer, trimer and tetramer, respectively. The oligomer of the present invention is available commercially from F2 Chemicals, Ltd.

The perfluorocarbon film-former is used in an amount from 0.1% up to an amount of less than 50%, preferably 10% up to an amount of less than 50%, more preferably from 20% to 45%, and most preferably from 30% to 40%.

Another optional component of the present invention is a gellant. The perfluoro compounds are combined with a fumed silica, or silica silylate, as the gellant. By "fumed silica" it is meant those high-surface area powdered silicas prepared by a pyrogenic process, e.g., during burning silicon tetrachloride in air (i.e., by the flame hydrolysis of silicon tetrachloride) and has a plurality of 99.8% or greater. In this process, submicron sized molten spheres of silica collide and fuse to form three dimensional, branched, chain-like aggregates, of approximately 0.1 to 0.5 microns in length. Cooling takes place very quickly, limiting the particle growth and ensuring the fumed silica is amorphous.

Fumed silicas are available in untreated form, or with a surface treatment to render the silica more hydrophobic. Although either type can be used, preferably the fumed silica used in the present invention is untreated. The surface area of the fumed silica is preferably between 90 to about 380 m2/g, and most preferably is between about 200 to about 380 m2/g. A particularly useful fumed silica is commercially available from Cabot Corporation under the trade name Cab-o-Sil M-5. The gellant is employed in an amount of about 0.5 to about 20% by weight of the total composition, and preferably is used in an amount of about 1% to about 10%, most preferably from about 1% to about 5%.

Co-gellants may also be used with the fumed silica. It is important to note that the co-gellant cannot function on its own in gelling the perfluoro compound, but can contribute to the gelling function and aid in reducing raspiness or dryness that might be experienced when using larger quantities of fumed silica. Particularly preferred co-gellants for the present invention are dimethicone crosspolymers. A wide variety of materials of this type are available commercially, for example from Shin-Etsu. Preferred for use in anhydrous systems of the invention are vinyl dimethicone crosspolymers, in powder form. A particularly preferred material is vinyl dimethicon/methicone silsesquioxane crosspolymer. In water-containing systems of the invention, it is preferred to use fluorinated dimethicone crosspolymers. Particularly preferred for this purpose is a combination of fluorinated dimethicone crosspolymers, namely trifluoropropyl cyclopentasiloxane/trifluoropropyl cyclotetrasiloxane/trifluoropropyl dimethicone crosspolymer combined with trifluoropropyl cyclopentasiloxane/PEG-10/trifluoropropyl dimethicone crosspolymer/trifluoropropyl cyclotetrasiloxane. In contrast to the anhydrous product, these materials are preferably incorporated into the formula in the form of a gel rather than a powder. The absolute amount of co-gellant, if employed, is not crucial, and can be present in an amount of from about 0.01 to about 10%, preferably from about 0.5 to about 5%, by weight of the crosspolymer. In relation to the amount of the primary gellant, the ratio of the two will normally be approximately 1:1, if the co-gellant is used, but the co-gellant may be used in a ratio as high as about 3 parts co-gellant to 1 part primary gellant with acceptable results.

In the embodiments and combinations described above, the compositions may be relatively simple, and, unlike traditional mascaras, substantially wax-free. By wax-free in the present context is meant a composition containing no more than 20%, preferably no more than 10%, more preferably no more than 5%, and most preferably, substantially no waxes.

In an alternate embodiment, the perfluorocarbon is used in an amount of greater than 50% by weight as the base of a typical pasty mascara composition. At that percentage level in this embodiment, as an additional ingredient, a fluorinated wax may be incorporated into the present invention to aid in uniform application of the present inventive composition over the keratinous fibers. It is important to note that non-fluorinated waxes are less compatible with the perfluoro compounds of the present invention and can result in the separation of the inventive composition into two layers. Therefore, fluorinated waxes are preferably used in the present invention. While not wishing to be bound by any theories, it is believed that the amount of fluorination in the perfluoro compounds of the present invention, render some fluorinated waxes incompatible, as seen in Example 3 below. It is further believed that the saponification value of the fluorinated wax is related to the compatibility of the wax with the perfluoro compound of the present invention. The saponification value of an oil or fat is a measure of the mean molecular weight of the component of glycerides or fatty acids and is defined as the number of milligrams of potassium hydroxide required to saponify 1 gram of oil or fat, i.e. to neutralize the free fatty acids and the fatty acids combined as acylglycerols. The saponification value is thus determined, among other known methods, by measuring the amount of excess potassium hydroxide remaining after the saponification. In the present invention, it is believed that waxes with a saponification value of less than 50, preferably less than 40 and most preferably less than 30 are compatible within the present invention. The most preferred wax in the present invention is fluorobehenyl alcohol, which has a saponification value of 30.

Examples of such waxes include but are not limited to diperfluorododecanediate and fluorobehenylalcohol. In the preferred embodiment, diperfluorododecanediate is used in an amount of from 2% to 40%, preferably from 5% to 30%, and most preferably from 10% to 20%.

As another nonessential, but sometimes desirable component, one or more types of pigments may be included to enhance the darkening of the keratinous fibers. The amount of pigment used is not critical, and will depend largely on the type and intensity of color desired. Ordinarily, the pigments will be used in an amount of about 1 to about 20% by weight. The types of pigments that are employed can be any that are ordinarily used for this purpose; for example, they may be organic, including natural colorants and synthetic monomeric and polymeric colorants. Exemplary organic pigments are phthalocyanine blue and green pigment, diarylide yellow and orange pigments and azo-type red and yellow pigments such as toluidine red, litho red, napthol red and brown pigments. Also useful are lakes, which are pigments formed by precipitation and absorption of organic dyes on an insoluble base, such as alumina, barium or calcium hydrates. Particularly preferred lakes are primary FD&C or D&C lakes and blends thereof. Stains, such as bromo dyes and fluorescein dyes can also be employed.

The pigments can also be inorganic, such as iron oxides (yellow, red, brown or black), ferric ammonium ferrocyanide (blue), manganese violet, ultramarine blue, chrome oxide (green), talc, lecithin modified talc, zeolite, kaolin, lecithin modified kaolin, titanium oxide (white), zinc oxide and mixtures thereof. Also useful are transparent metal oxide-coated silica beads. Metal oxides, particularly iron and titanium oxides, are preferred pigments in the composition of the invention. The pigments employed may be coated or uncoated. A particularly preferred type of pigment is an iron oxide, such as Black NF available from, for example, KOBO, in South Plainfield, N.J.

The composition of the present invention is preferably an anhydrous coating composition containing either at least one perfluoro compound alone, or in combination with a perfluorocarbon film-former. The composition may also be incorporated into a traditional anhydrous or water-based mascara composition.

Method of Darkening Keratinios Fibers

The present inventive compositions are particularly useful as products useful as methods of darkening the keratinous fibers of humans through topical application of the inventive composition. Preferably, the compositions is used in a mascara composition for darkening eye lashes.

Such methods comprise administering or topically applying to the keratinous fibers a safe and effective amount of the composition of the present invention. The amounts of the components in the compositions will vary depending upon the level of darkening desired and the individual's keratinous fiber type. The method of the present invention is suitable for daily use.

It is suggested as an example that topical application range from about once per day to about three times daily, preferably twice daily.

The invention is further illustrated by the following non-limiting examples.

EXAMPLE 1

The following formula illustrates compositions of the invention in which perfluoro compounds of the present invention are incorporated into a mascara composition; however it is noted that the perfluoro compounds may be used alone as a coating or in combination with other perfluoro compounds as listed hereinabove without incorporation into a mascara composition.

| Material | Weight % |
| --- | --- |
| Diperflurododecanediate | 20.00% |
| Flutec PC11 (Perfluoroperhydrophenathrene) | 50.00% |
| Flutec PC3 (Perfluoro 1,3 Dimethylcyclohexane) | 19.05% |
| Cab-O-Sil M-5 (Silica) | 0.75% |
| Propyl Paraben | 0.2% |
| Black NF(Iron Oxides-Black Pigment) | 10% |

EXAMPLE 2

This example provides comparative examples of the darkening effects of various mascara compositions, with and without the present inventive compositions. FIGS. 1-3 herein depict the L (Lightness) value of the compositions. The compositions are measured for the L value using a spectrophotometer, a low L value representing a lighter color. Specifically, FIG. 1 shows the lowest L-value using the inventive composition, at a value of 18. In FIG. 2, the effect of specific perfluoro compounds are depicted, with the inventive composition comprising Flutec® providing the lowest L value at 20.26.

EXAMPLE 3

This example provides comparative examples of fluorinated waxes in combination with the perfluoro compound of the present invention. As seen by Table 1, only the diperfluorododecanediate and the fluorobehenylalcohol were compatible with the perfluoro compound, Flutec PC11, to yield a stable composition that did not separate. Also as seen in Table 1, fluorobehenylalcohol is tested at two different concentrations.

TABLE 1

Comparative data for waxes

| Combination | Weight % | Compatibility |
| --- | --- | --- |
| FLUOROCANDELILLA (5 OR 8% FLUORINATION) | 50 | Separation, two layers, not compatible |
| FLUTEC PC11 | 50 | |
| FLUOROCARNAUBA(5 OR 8% FLUORINATION) | 50 | Separation, two layers, not compatible |
| FLUTECPC11 | 50 | |
| DIPERFLUORODODECANEDIATE | 50 | One layer, no separation, compatible |
| FLUTEC PC11 | 50 | |
| FLUOROBEHENYLALCOHOL (8% FLUORINATION) | 50 | One layer, no separation, some sweating observed |

TABLE 1-continued

Comparative data for waxes

| Combination | Weight % | Compatibility |
|---|---|---|
| FLUTEC PC11 | 50 | |
| FLUOROBEHENYLALCOHOL (8% FLUORINATION) | 60 | One layer, no separation, compatible, no sweating observed |
| FLUTEC PC11 | 40 | |

It should be understood that the specific forms of the invention herein illustrated and described are intended to be representative only. Changes, including but not limited to those suggested in this specification, may be made in the illustrated embodiments without departing from the clear teachings of the disclosure. Accordingly, reference should be made to the following appended claims in determining the full scope of the invention.

What is claimed is:

1. An anhydrous cosmetic or pharmaceutical composition for coating keratinous fibers, the composition comprising more than 50% of at least one perfluoro compound selected from the group consisting of perfluorocycloalkanes, hydrofluoroethers and perfluoromorpholines.

2. The composition of claim 1 in which the perfluoro compound is a perfluorocycloalkane or hydrofluoroether.

3. The composition of claim 1 further comprising a fluorinated wax.

4. The composition of claim 2 in which the perfluorocycloalkane comprises is selected from the group consisting of perfluorodecalin, perfluoromethyldecalin, perfluorohydrophenanthrene, or perfluoro-1,3-dimethylcyclohexane, or a combination thereof.

5. The composition of claim 4 in which the perfluoro compound is a perfluoro-1,3-dimethylcyclohexane.

6. The composition of claim 1 further comprising a perfluorocarbon film-former which is a fluorinated oligomer.

7. The composition of claim 6 wherein the fluorinated oligomer is a byproduct of perfluorotetradecahydrophenanthrene.

8. A cosmetic or pharmaceutical composition for coating keratinous fibers comprising more than 50% of at least one perfluoro compound and at least one perfluorocarbon film-former.

9. The composition of claim 8 in which the perfluoro compound is selected from the group consisting of perfluorocycloalkanes, hydrofluoroethers, perfluoromorpholines, and perfluoroalkanes.

10. The composition of claim 9 in which the perfluoro compound is a perfluorocycloalkane or hydrofluoroether.

11. The composition of claim 8 further comprising a wax.

12. The composition of claim 10 in which the perfluorocycloalkane is selected from the group consisting of perfluorodecalin, perfluoromethyldecalin, perfluorohydrophenanthrene, or perfluoro-1,3-dimethylcyclohexane, or a combination thereof.

13. The composition of claim 10 in which the perfluoro compound is a perfluoro-1,3-dimethylcyclohexane.

14. The composition of claim 8 wherein the perfluorocarbon film-former is a fluorinated oligomer.

15. The composition of claim 8 wherein the fluorinated oligomer is a byproduct of perfluorotetradecahydrophenanthrene.

16. A cosmetic or pharmaceutical composition for coating keratinous fibers comprising at least one perfluoro compound selected from the group consisting of perfluorocycloalkanes, hydrofluoroethers and perfluoromorpholines and at least one fluorinated oligomer.

17. The composition of claim 16 in which the perfluoro compound is a perfluorocycloalkane or hydrofluoroether.

18. The composition of claim 17 in which the perfluorocycloalkane is selected from the group consisting of perfluorodecalin, perfluoromethyldecalin, perfluorohydrophenanthrene, or perfluoro-1,3-dimethylcyclohexane, or a combination thereof.

19. The composition of claim 16 in which the perfluoro compound is a perfluoro-1,3-dimethylcyclohexane.

20. The composition of claim 16 wherein the fluorinated oligomer is a byproduct of perfluorotetradecahydrophenanthrene.

21. A method for darkening keratinous fibers comprising the step of applying to the keratinous fibers an anhydrous composition comprising at least one perfluoro compound selected from the group consisting of perfluorocycloalkanes, hydrofluoroethers and perfluoromorpholines.

22. The method of claim 21 wherein the perfluoro compound is a perfluorocycloalkane or hydrofluoroether.

23. The method of claim 21 wherein the composition further comprises a wax.

24. The method of claim 21 in which the perfluorocycloalkane is selected from the group consisting of perfluorodecalin, perfluoromethyldecalin, perfluorohydrophenanthrene, or perfluoro-1,3-dimethylcyclohexane, or a combination thereof.

25. The method of claim 21 in which the perfluoro compound is a perfluoro-1,3-dimethylcyclohexane.

26. The method of claim 21 wherein the composition further comprises a fluorinated oligomer.

27. The method of claim 26 wherein the fluorinated oligomer is a byproduct of perfluorotetradecahydrophenanthrene.

* * * * *